US005161680A

United States Patent [19]

Badgley

[11] Patent Number: 5,161,680
[45] Date of Patent: Nov. 10, 1992

[54] PROTECTIVE DEVICE

[76] Inventor: Laurence E. Badgley, 1020 Foster City Blvd., Foster City, Calif. 94404

[21] Appl. No.: 692,450

[22] Filed: Apr. 5, 1991

[51] Int. Cl.[5] ...................... A45C 15/00; B65D 81/24; A24F 25/00; A61L 9/04

[52] U.S. Cl. ...................................... 206/38; 206/205; 239/36; 239/44; 239/51.5

[58] Field of Search ........................ 206/38, 205, 527; 239/34, 36, 44, 51.5

[56] References Cited

U.S. PATENT DOCUMENTS

| | | | |
|---|---|---|---|
| 168,972 | 10/1875 | Dayton | 239/34 |
| 1,675,940 | 7/1928 | Lewis | 206/219 |
| 1,991,938 | 2/1935 | Houghton | 239/34 |
| 2,141,402 | 12/1938 | Muller | 239/36 |
| 2,342,406 | 2/1944 | Latta et al. | 206/205 |
| 2,766,066 | 10/1956 | Hopson et al. | 239/34 |
| 3,685,734 | 8/1972 | Paciorek et al. | 206/0.5 |
| 3,702,677 | 11/1972 | Heffington | 206/205 |
| 4,889,285 | 12/1989 | Locko | 239/34 |

*Primary Examiner*—Paul T. Sewell
*Assistant Examiner*—M. D. Patterson
*Attorney, Agent, or Firm*—T. R. Zegree

[57] ABSTRACT

A protective device attachable to outer garment for self-protection of a person against criminal attack comprises an ornamental, pliable, hollow body having inserted therein an easily breakable ampul containing a volatile foul smelling fluid which is emitted through apertures in the body of the device when the ampul is fractured by squeezing said body. When worn by a woman, the device is particularly useful for deterring an assault by a rapist.

16 Claims, 1 Drawing Sheet

PROTECTIVE DEVICE

BACKGROUND OF THE INVENTION

This invention pertains to a protective device. More particularly, the invention relates to a self-protective device for use in deterring a criminal assault on a person, especially a woman.

As reported by news media, incidents of assaults on woman, particularly rapes, occur every day in parks, college campuses and their residences. For example, Stanford University has recently reported, as a result of a 3-year survey of 2400 students, that one-third of the women students have been raped on the University campus. In addition, a recent release by the U.S. Senate Judiciary Committee reports that more than 100,000 woman were raped in 1990 and woman are in greater peril now from attack than they have ever been. Accordingly, it becomes imperative that woman be provided with a reliable means of protection which would incapacitate the attacker and interrupt his assault.

Various types of devices for self-protection of a woman from threat of rape or other bodily injury intended by a man have been suggested. Such devices include aerosol weapons containing tear or nerve gas. However, their use is unlawful in many states. Other non-lethal or lethal handguns and a variety of common household objects have been used by woman at the time of being confronted by a criminal. However it is often difficult to find an object which could be used immediately as a defensive weapon. While patent references relating to the subject of personal protection against attackers are scarce, U.S. Pat. No. 4,698,844 to Miyada relates to an anti-crime device in the form of a spike-needle comprising steel wires for attachment to fur coats or similar garments. A book entitled "Are you a target" by Judith Fein (1981) explores ways of preventing attacks against the will of an intended victim.

While the above-mentioned devices are useful but not entirely adequate as they are often not readily available when needed for self-protection, the present invention provides a new and simple approach for a protective device especially developed to deter or prevent an assault by a rapist or another type of a criminal. The device of this invention overcomes the disadvantages of prior practices and offers an added advantage of being activated at once by a woman in the event of an unexpected attack.

OBJECTS OF THE INVENTION

In view of the foregoing, it is the principal object of the invention to provide an improved protective device specifically adapted for prevention of a criminal attack on a woman by an assailant, particularly a rapist.

It is another object of the present invention to provide a small anti-crime and anti-rape device containing a repellent, malodorous fluid, the device being adapted for wearing by a person to be used for immediate preventive action when needed by quick emission of such fluid.

Still another object of this invention is the provision of a device in the form of a decorative item for attachment to woman's outer garment, the device being highly effective in deterring an assault by a rapist.

Still another object of the invention is to provide a pliable device for personal safety, as described herein, which can be manufactured in large quantities at a low cost from readily available materials.

These and other objects of the invention will become more fully apparent from the following description when considered in conjunction with the accompanying drawings.

BRIEF SUMMARY OF THE INVENTION

In accordance with the invention described herein in its preferred embodiment, there is provided a protective device for deterring a forcible attack by an assailant against a person, said device being attachable to a garment or another accessory worn by said person, comprising: a pliable and flexible body having a cavity and an opening adapted for insertion of an ampul into said cavity; an easily breakable ampul containing a volatile malodorous fluid, said ampul being placed within said cavity; a closing means shaped to fit said opening; at least one duct in said closing means or in said body for air passage therethrough; and a fastening means secured to external surface of said body.

BRIEF DESCRIPTION OF THE DRAWINGS

In the accompanying drawings wherein like reference characters designate corresponding elements throughout the views thereof.

Figure 5:
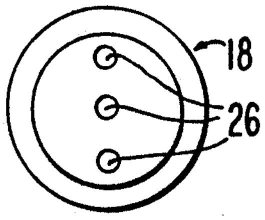
Figure 6:
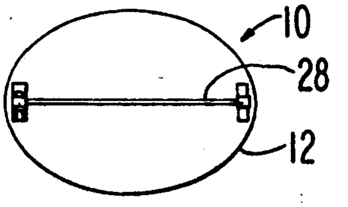

FIG.. 4 is an enlarged cross-sectional view of the closing means;

FIG. 5 is an enlarged side view of the closing means;

FIG. 6 is a rear view of the device showing a clasp member; and

Figure 7:
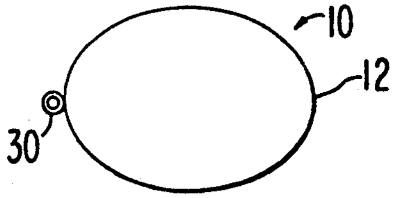

FIG. 7 is a rear view of the device with an eyelet secured thereto.

DETAILED DESCRIPTION OF THE INVENTION

Figure 1:
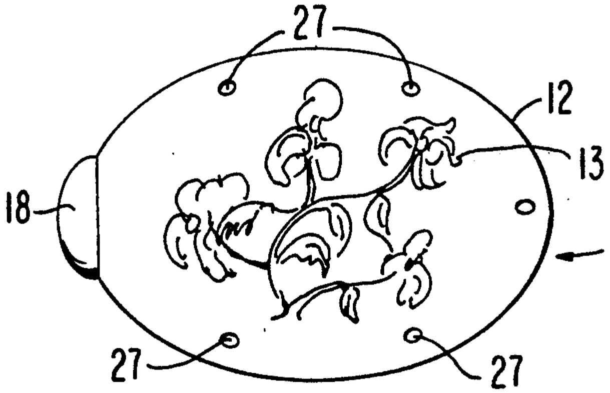
FIG. 1 is a front view of the protective device in operative position.

Referring now to the drawings, protective device 10, as illustrated in FIG. 1, is designed to be worn by a woman as an attachment to a garment, such as a blouse, a dress or a coat by a suitable fastening means employed for jewelry articles, such as a clasp 28 shown in FIG. 6 or an adhesive tape, such as Velcro. The device may also be attached to a jewelry item worn by a woman, such as a bracelet or a necklace by means of an eyelet 30 shown in FIG. 7 or any other suitable fastener. The wearing of device 10 having appearance of an accessory or an article of jewelry on the outer side of a garment is intended to be inconspicuous so that an assailant approaching his selected victim will not be alerted by its deterrent and protective function. Accordingly, device 10 may be formed in various shapes, such as oval, oblong, round, rectangular, etc. and the body 12 may be translucent, opaque or tinted in a variety of colors. Moreover, the outer front surface of body 12, such body being made of a pliable, flexible and resilient material, such as plastic or rubber, may be provided with a decorative ornament, such as a floral design 13, as shown by way of an example in FIG. 1, or any other artistic pattern. Device 10 may also be made in the form of an animal, such as a cat, a dog, a bird, etc., as well as in the form of a brooch, a pin, an emblem and the like.

Device 10 is made in a relatively small size, generally from 1 in. to 3 inches or even somewhat longer, if desired.

Figure 2:
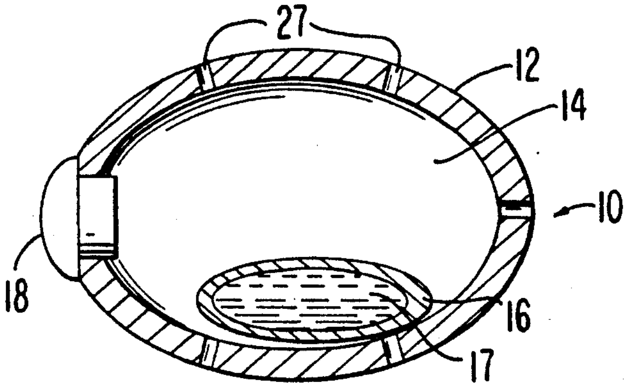
FIG. 2 is a cross-sectional view of the device with a closing means and an ampul placed therein.
Figure 3:
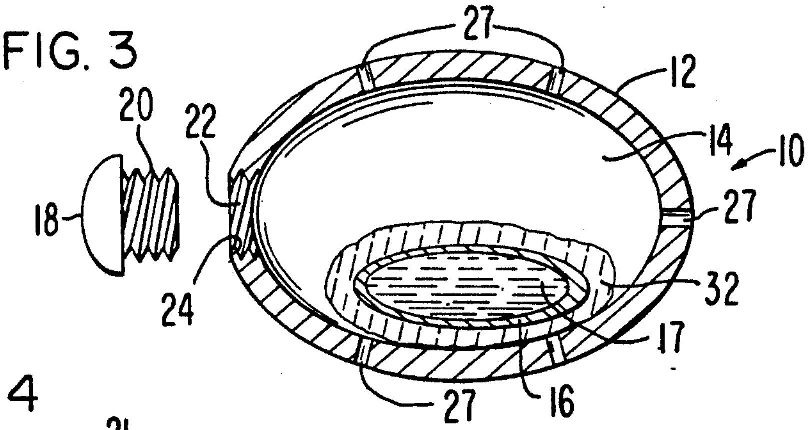
FIG. 3 is a cross-sectional view of the device showing a covered ampul and a threaded closing means detached from the device.

It is one of the important features of the invention that device 10 is hollow, as it comprises an inner cavity 14 extending substantially throughout the length of body 12, as illustrated in FIG. 2 and FIG. 3. Cavity 14 is provided with an opening 22 specifically adapted for insertion of ampul 16 therein. It will be understood, therefore, that the size of opening 22 must be somewhat larger than the outer diameter of ampul 16 to permit an easy insertion thereof into the cavity 14. Ampul 16 is in the form of an elongate, generally cylindrical, sealed and easily breakable container made of thin glass or a similar plastic material, such as usually employed in the manufacture of ampuls containing liquid medications for hypodermic injections.

It is another important feature of the present invention that ampul 16 is filled with a non-lethal, volatile, foul-smelling fluid 17 which is emitted instantaneously into cavity 14 when ampul 16 is broken and then rapidly thereafter into the area adjacent device 10 through a plurality of air passages or ducts 26 disposed in closing means 18 and/or similar ducts 27 in body 12 arranged in several locations thereof.

Fluid 17, which is characterized by a strong, unpleasant odor, may comprise one of the known gaseous or liquid chemical substances, preferably a sulfur-containing compound, such as a mercaptan, including methanethiol, mercaptoethanol, hydrogen sulfide and others. Any fluid of this type is encapsulated by any well known proceddure in ampul 16 which is impermeably sealed so that it will not release the foul odor from fluid 17 until it is fractured.

Figure 4:
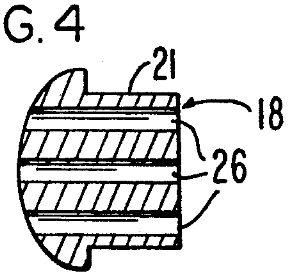

Closing means 18, illustrated in FIGS. 3 and 4 in greater detail, is shaped to fit opening 22 which is dimensioned specifically to form an airtight seal therewith. Closing means 18 is generally in the form of a plug, such as a screw cap having an externally threaded portion 20 which is adapted for threading engagement with inner surface 24 of opening 22 which is threaded correspondingly. Other types of closing means 18, such as a plug, the portion 21 of which has a smooth surface adapted for engagement with the circular smooth wall of opening 22, are likewise suitable for insertion into opening 22.

Closing means 18 is provided with at least one duct 26 or, preferably, with a plurality thereof, as shown in FIGS. 4 and 5, wherein three ducts are included by way of an example. Each duct 26 extends throughout the length of closing means 18, thereby providing air passage between cavity 14 and the outside of closing means 18. A plurality of similar ducts 27 may also be provided in body 12 extending throughout the thickness thereof and being arranged in several locations, as shown in FIGS. 1, 2 and 3. The provision of ducts 26 or 27 is essential for the function of the invention to permit the malodorous gas or vapor from fluid 17 to escape from cavity 14 therethrough when ampul 16 is fractured. Although the size of ducts 26 and 27 is not critical, their diameter from about 1/32 in. to about ¼ in. is generally satisfactory.

In order to prevent a too rapid outward flow of fluid 17 when in the form of a liquid from cavity 14 through ducts 26 or 27, ampul 16 may be covered or overlaid with an absorbent fibrous or the like material 32 which would retain a portion of fluid 17 for a somewhat longer period of time before release of its stench into the area outside of device 10.

It will be apparent from the foregoing description that I have devised a novel, self-protective device especially adapted for a readily accessible use in deterring an attack on a woman, particularly an attempt of rape. When the device of this invention is placed in operative position by a person wearing it as described hereinabove, it is sufficient to apply pressure thereon by merely squeezing its body by hand to flex it causing the ampul housed in the interior thereof to fracture, thereby releasing immediately a foul odor on the outside of the device. Such odor is so bad and disagreeable to the attacker that it will interrupt his violent assault on the intended victim due to impairment of his agressive attempt and a temporary sexual dysfunction thus preventing the attacked woman from being raped or otherwise forcefully overwhelmed by man's physical strength. The device of my invention is particularly useful for wearing by joggers and woman walking alone after dark or being alone in their homes, thereby offering them personal security. In view of simplicity of its design and availability of the materials required for its construction, the device may be produced inexpensively in large volume.

It will be understood that changes or modifications in the form or in the constructional details of my invention as herein described may be made without departing from the spirit thereof or the scope of the claims which follow.

I claim:

1. A protective device for deterring a forcible attack by an assailant against a woman wearing said device comprising in combination:
   - a pliable and flexible body having a cavity and an opening in said body;
   - a breakable ampul containing a volatile malodorous fluid, said ampul being insertable into said cavity through said opening;
   - a removable closing means shaped to fit said opening for an airtight seal therewith;
   - at least one duct in said closing means extending throughout the length of said closing means for unobstructed air passage therethrough; and
   - a fastening means secured to external surface of said body for attachment of said device to a garment worn by said woman.

2. A protective device of claim 1 wherein said body is made from a plastic material.

3. A protective device of claim 1 wherein said cavity extends through the length of said body.

4. A protective device of claim 1 wherein said cavity is larger than said ampul.

5. A protective device of claim 1 wherein said ampul is made of thin glass material.

6. A protective device of claim 1 wherein said fluid comprises a sulfur compound.

7. A protective device of claim 6 wherein said sulfur compound comprises a mercaptan.

8. A protective device of claim 1 wherein said opening is dimensioned for tight insertion of said closing means therein.

9. A protective device of claim 1 wherein said closing means comprises longitudinal ducts and an externally threaded screw cap adapted for threading engagement with inner surface of said opening.

10. A protective device of claim 1 wherein said closing means comprises a plug having a smooth surface for engagement with a smooth inner surface of said opening.

11. A protective device of claim 1 wherein said body comprises a plurality of ducts extending throughout the thickness thereof for passage of foul odor from said fluid upon breaking said ampul.

12. A protective device of claim 1 wherein said closing means comprises a plurality of ducts for passage of foul odor from said fluid upon breaking said ampul.

13. A protective device of claim 1 wherein said fastening means comprises a clasp.

14. A protective device of claim 1 wherein outer surface of said body comprises a decorative ornament.

15. A protective device of claim 1 wherein an absorbent material is placed in said cavity adjacent said ampul.

16. A protective device of claim 1 wherein said device is attachable by said fastening means to an accessory which is attached to a garment worn by the woman.

* * * * *